(12) United States Patent
Crosby et al.

(10) Patent No.: US 9,976,972 B2
(45) Date of Patent: May 22, 2018

(54) THERMAL CONTROL APPARATUS

(71) Applicant: THERMO GAMMA-METRICS PTY LTD, Adelaide Airport (AU)

(72) Inventors: Bryan John Crosby, Adelaide (AU); Simon Liemar, Adelaide (AU)

(73) Assignee: THERMO GAMMA-METRICS PTY LTD, Adelaide Airport (AU)

( * ) Notice: Subject to any disclaimer, the term of this patent is extended or adjusted under 35 U.S.C. 154(b) by 185 days.

(21) Appl. No.: 14/969,766

(22) Filed: Dec. 15, 2015

(65) Prior Publication Data

US 2017/0167989 A1    Jun. 15, 2017

(51) Int. Cl.
| | |
|---|---|
| F25B 9/04 | (2006.01) |
| G01N 23/223 | (2006.01) |
| F15D 1/00 | (2006.01) |
| F28F 13/02 | (2006.01) |
| F28F 13/12 | (2006.01) |
| G01N 23/203 | (2006.01) |
| H01J 35/18 | (2006.01) |
| H05G 1/02 | (2006.01) |

(52) U.S. Cl.
CPC .......... *G01N 23/223* (2013.01); *F15D 1/009* (2013.01); *F15D 1/0015* (2013.01); *F28F 13/02* (2013.01); *F28F 13/12* (2013.01); *G01N 23/203* (2013.01); *H01J 35/18* (2013.01); *H05G 1/02* (2013.01); *G01N 2223/076* (2013.01); *G01N 2223/322* (2013.01); *G01N 2223/635* (2013.01)

(58) Field of Classification Search
CPC .......... F28F 13/06; F28F 9/22; F28F 2265/10; F28F 1/42; F28D 15/00; F28D 1/06

USPC ................................ 378/44; 65/5; 165/109.1
See application file for complete search history.

(56) References Cited

U.S. PATENT DOCUMENTS

| | | | |
|---|---|---|---|
| 8,937,482 B1 | 1/2015 | Lemczyk | |
| 2005/0257533 A1 | 11/2005 | Gunawardana et al. | |
| 2008/0209914 A1* | 9/2008 | De Wergifosse | F25B 9/04 62/5 |
| 2011/0173994 A1 | 7/2011 | Chang et al. | |

FOREIGN PATENT DOCUMENTS

CN         103808746 A       5/2014

OTHER PUBLICATIONS

Vortex Coolers—Stratus brochure, Apr. 15, 2015, 3 pages.
Vortex Tubes—Airtx International brochure, 2 pages, downloaded Jan. 9, 2014.

* cited by examiner

*Primary Examiner* — Don Wong
(74) *Attorney, Agent, or Firm* — William R. McCarthy, III

(57) ABSTRACT

A thermal control apparatus adapted for use with a pressurized air supply for controlling temperature of a component includes a vortex tube having an inlet adapted for connection with the pressurized air supply, a cold air outlet, and a hot air outlet, and a heat exchanger in fluid communication with the cold air outlet of the vortex tube, the heat exchanger being in thermal contact with the component and thereby controlling the temperature of the component. The heat exchanger further includes a post-heat-exchange exhaust air outlet in fluid communication with an exhaust air inlet adapted to direct the exhaust air along an outside of the vortex tube.

30 Claims, 9 Drawing Sheets

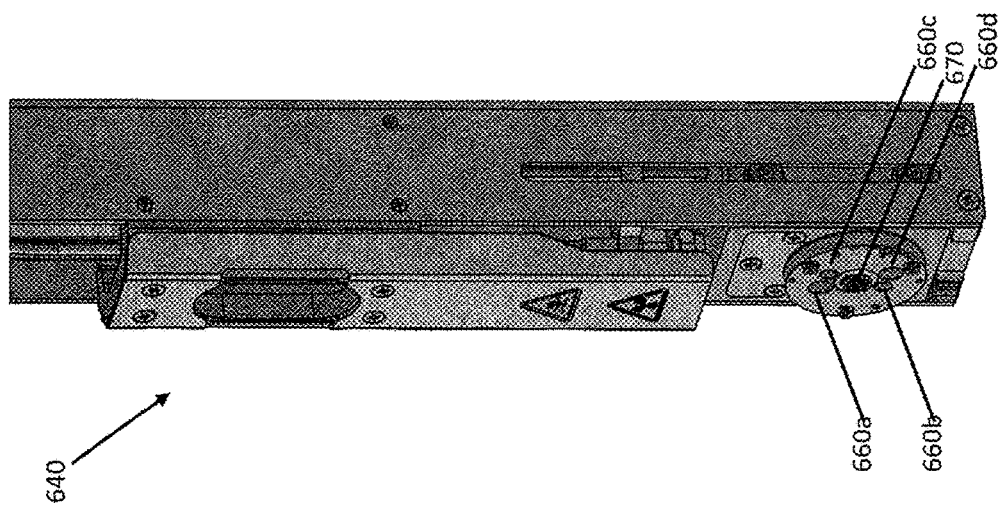

US 9,976,972 B2

THERMAL CONTROL APPARATUS

FIELD OF THE INVENTION

The invention is generally related to thermal control apparatus and method.

BACKGROUND

In mineral ore processing plants associated with mining operations, online sampling and analysis stations typically provide continuous in-stream analysis of composite samples for metallurgical accounting, enabling plant operators to follow and respond to process trends in real time. Such sampling and analysis stations generally include an inlet, an outlet, a stirrer, and a dedicated immersion probe analyzer mounted into the final tank of a full-flow sampling station designed to present to the analyzer a representative sample of the main ore slurry stream. The integrated immersion probe analyzer provides simultaneous analysis of typically up to 20 elements and percent solids in the slurry. Elements from calcium (Ca) to uranium (U) in the periodic table are measured by the immersion probe analyzer that typically includes a multi-element probe (MEP) using X-ray fluorescence (XRF), a proven and robust technology for plant environments.

In an XRF measurement using the immersion probe analyzer, the MEP uses an X-ray source to excite fluorescent X-rays from elements in the mineral ore slurry. Each element in the ore slurry emits fluorescent X-rays of an energy and intensity that is characteristic of that element and its concentration. Fluorescent and scattered X-rays from the ore slurry impinge on the detector of the MEP to produce small electrical pulses that are shaped, amplified, and counted. The peak amplitude of the pulse is proportional to the energy of the incident X-ray. The scattered X-rays are used to provide measurements of the ore slurry density. The number of X-rays is proportional to the elemental concentration in the ore slurry.

The detector of the MEP is typically a silicon drift detector (SDD). A typical detector configuration includes an SDD chip having a hot side in thermal contact with a Peltier-cooled heat sink that provides heat exchange with the SDD chip. An alternative approach to cooling the heat sink includes flowing liquid nitrogen ($LN_2$) through the heat sink. Liquid nitrogen cooling, however, requires cryogenic storage and refilling.

Another alternative approach to cooling and controlling the temperature of an electronic component mounted on a heat sink, described in U.S. Pat. No. 8,937,482 B1, hereby incorporated by reference in its entirety (however, where anything in the incorporated reference contradicts anything stated in the present application, the present application prevails), is to flow the cold air output of a vortex tube through the heat sink.

As shown in FIG. 1, a vortex tube 100 takes in a pressurized air supply through an inlet 110 and produces a cold air output 120 and a hot air output 130. Depending on inlet air pressure and fraction of cold air output that is controlled by adjusting the hot air flow rate using control valve 140, the cold air temperature can be as low as −40° C., and the hot air temperature can be as high as 110° C. The surface of the vortex tube also becomes nearly as hot as the hot air output during operation. Additionally, a vortex tube produces very loud noise, in excess of 100 dBA, during operation. The high surface and hot air output temperatures and noise pose significant safety concerns for nearby operators.

Therefore, there is a need for a thermal control apparatus that reduces or eliminates the problems described above.

SUMMARY

In one embodiment, a thermal control apparatus adapted for use with a pressurized air supply for controlling temperature of a component includes a vortex tube having an inlet adapted for connection with the pressurized air supply, a cold air outlet, and a hot air outlet, and a heat exchanger in fluid communication with the cold air outlet of the vortex tube, the heat exchanger being in thermal contact with the component and thereby controlling the temperature of the component. The heat exchanger further includes a post-heat-exchange exhaust air outlet in fluid communication with an exhaust air inlet adapted to direct the exhaust air along an outside of the vortex tube. The component can be a hot side of a silicon drift detector, wherein the temperature of the hot side of the silicon drift detector is controlled to a set temperature, such as 15° C.

In some embodiments, the thermal control apparatus can additionally include a first muffler stage including an inner cylinder disposed around the vortex tube, the inner cylinder being in fluid communication with the exhaust air inlet, such that the exhaust air flows through the inner cylinder. The inner cylinder can be concentric with the vortex tube. In certain embodiments, the exhaust air flows through the inner cylinder in a direction from the vortex tube inlet toward the hot air outlet, and the apparatus additionally includes a second muffler stage including an outer cylinder in fluid communication with the hot air outlet. The outer cylinder can be concentric with the inner cylinder. In some embodiments, the outer cylinder can include a foam cylinder. In certain embodiments, the outer cylinder can further include a plurality of outlet apertures. The outlet apertures can have a diameter in a range of between 5 mm and 10 mm, such as 8 mm. In some embodiments, the thermal control apparatus can further include an enclosure housing the heat exchanger, wherein the vortex tube and exhaust air outlet are located outside the enclosure.

In another embodiment, a method of controlling temperature of a component includes supplying pressurized air into an inlet of a vortex tube having a cold air outlet and a hot air outlet, flowing cold air from the cold air outlet of the vortex tube to a heat exchanger that is in thermal contact with the component, and thereby controlling the temperature of the component, flowing post-heat-exchange exhaust air along an outside of the vortex tube, and combining the exhaust air with the hot air. The method further includes flowing the combined air to an exhaust air outlet.

In some embodiments, the method further includes flowing the exhaust air through a first muffler stage including an inner cylinder disposed around the vortex tube, the inner cylinder being in fluid communication with the exhaust air inlet, such that the exhaust air flows through the inner cylinder. In certain embodiments, the method further includes flowing the exhaust air through the inner cylinder in a direction from the vortex tube inlet toward the hot air outlet, and flowing the combined air through a second muffler stage including an outer cylinder in fluid communication with the hot air outlet. In some embodiments, flowing the combined air can generate a noise level of less than or equal to 80 dBA. In certain embodiments, the method further includes locating the heat exchanger in an enclosure, and locating the vortex tube and exhaust air outlet outside the enclosure.

In yet another embodiment, an XRF immersion probe analyzer includes a probe head immersible into and resistant to an ore slurry, the probe head including an X-ray transparent window, a probe that includes at least one X-ray source that emits X-rays toward a sample through the window, a silicon drift X-ray fluorescence (XRF) detector that detects X-ray radiation backscattered from the sample through the window, the silicon drift detector (SDD) having a hot side, a vortex tube having an inlet adapted for connection with the pressurized air supply, a cold air outlet, and a hot air outlet, and a heat exchanger in fluid communication with the cold air outlet of the vortex tube, the heat exchanger being in thermal contact with the hot side of the SDD and thereby controlling the temperature of the hot side of the SDD, the heat exchanger further including a post-heat-exchange exhaust air outlet in fluid communication with an exhaust air inlet adapted to direct the exhaust air along an outside of the vortex tube. The temperature of the hot side of the SDD can be controlled to a set temperature, such as 15° C. The vortex tube and muffler stages are as described above.

The invention has many advantages, such as reducing the noise level and lowering the temperature of the vortex tube surface and the temperature of the hot air output during operation.

BRIEF DESCRIPTION OF THE DRAWINGS

FIG. 6D is a perspective view of the probe shown in FIG. 6C.

Like reference numerals refer to corresponding parts throughout the several views of the drawings.

DETAILED DESCRIPTION OF EMBODIMENTS

Figure 1:
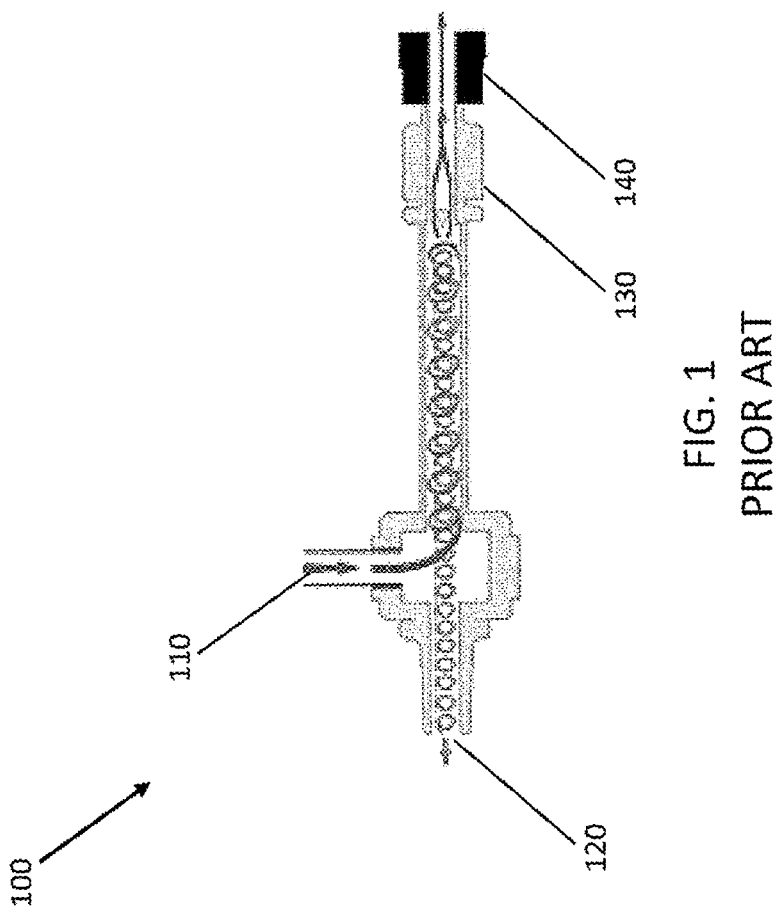
FIG. 1 is a schematic illustration of a cross section of a prior art vortex tube.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it will be understood that any list of such candidates or alternatives is merely illustrative, not limiting, unless implicitly or explicitly understood or stated otherwise. In addition, unless otherwise indicated, numbers expressing quantities of ingredients, constituents, reaction conditions and so forth used in the specification and claims are to be understood as being modified by the term "about".

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

Figure 2:
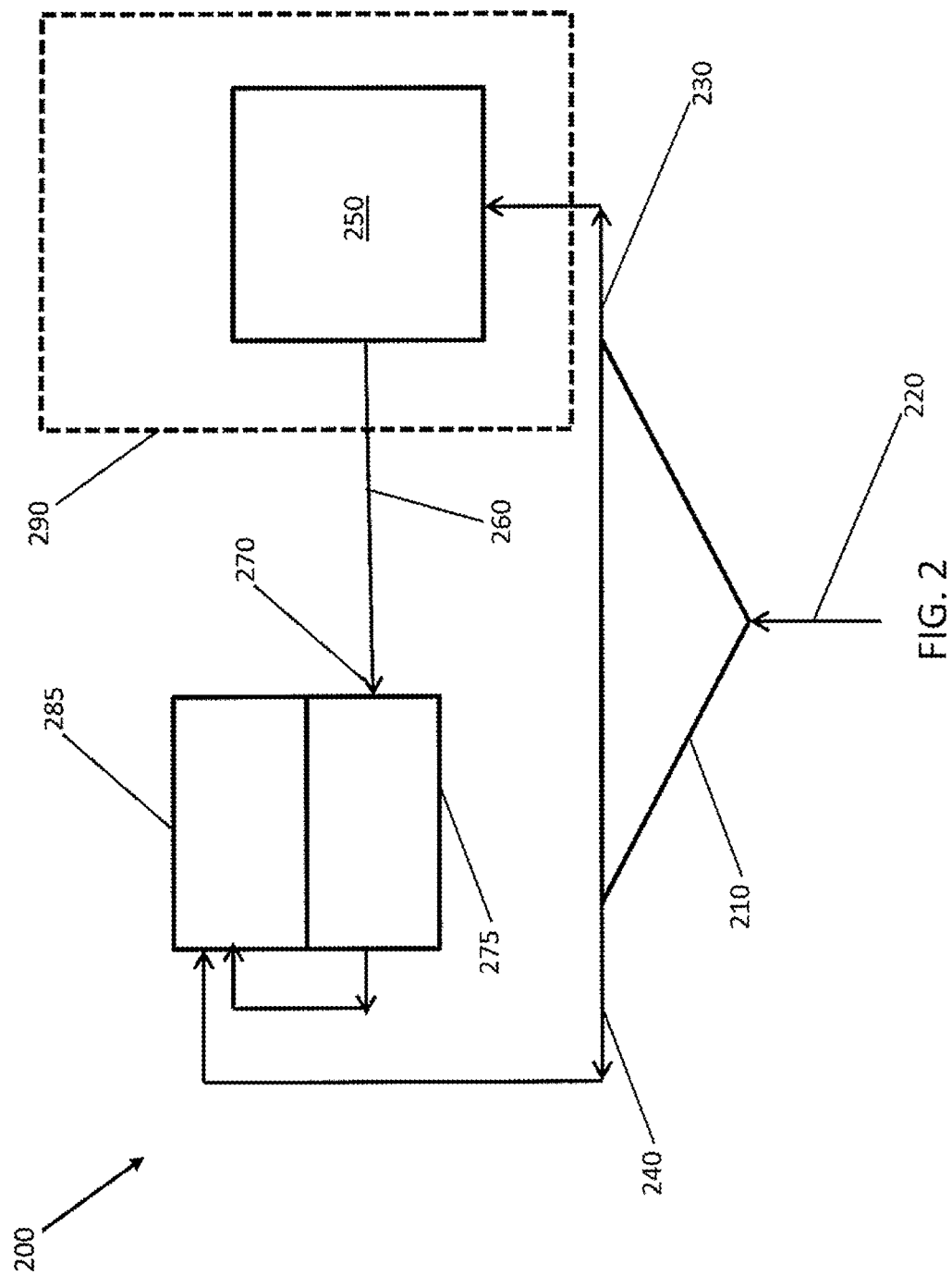
FIG. 2 is a flow diagram of an exemplary embodiment of a thermal control apparatus according to the invention.

In one embodiment schematically illustrated in FIG. 2, a thermal control apparatus 200 adapted for use with a pressurized air supply for controlling temperature of a component (shown in FIG. 3B) includes a vortex tube 210 having an inlet 220 adapted for connection with the pressurized (e.g., 6 atm) air supply, a cold air outlet 230, and a hot air outlet 240, and a heat exchanger 250 in fluid communication with the cold air outlet 230 of the vortex tube 210, the heat exchanger 250 being in thermal contact with the component and thereby controlling the temperature of the component. The heat exchanger 250 further includes a post-heat-exchange exhaust air outlet 260 in fluid communication with an exhaust air inlet 270 adapted to direct the exhaust air along an outside of the vortex tube 210 as described further below.

Figure 3B:
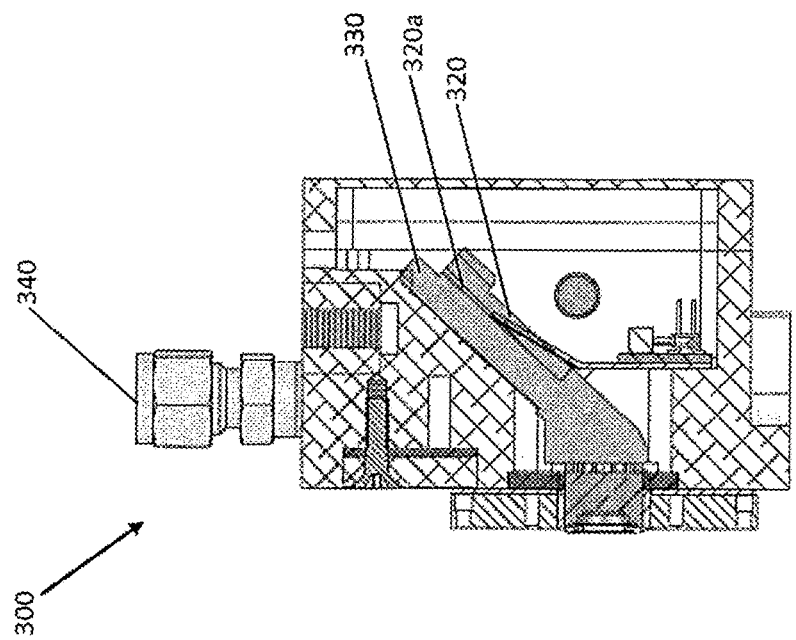
FIG. 3B is a cross section along line A-A of the silicon drift X-ray fluorescence (XRF) detector shown in FIG. 3A including an exemplary embodiment of a heat exchanger according to the invention.
Figure 3A:
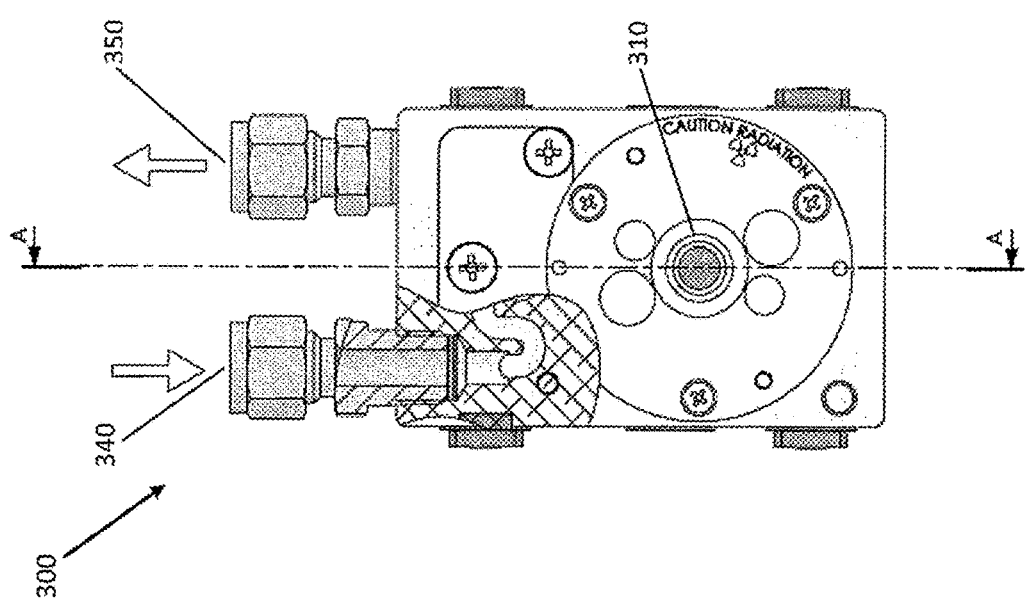
FIG. 3A is a front view of a silicon drift X-ray fluorescence (XRF) detector.

As shown in FIGS. 3A and 3B, a silicon drift detector (SDD) 300 includes a window 310, typically made of beryllium (Be), and an SDD chip 320, which is an electronic component that has a hot side 320a (see FIG. 3B) in thermal contact with a heat exchanger 330 that is cooled by cold air from the vortex tube described below. The cold air flows into the SDD 300 through the cold air inlet 340 and out through the post-heat-exchange exhaust air outlet 350. The temperature of the hot side 320a of the SDD chip 320 is controlled to a set temperature, such as 15° C.

Turning back to FIG. 2, the thermal control apparatus 200 can additionally include a first muffler stage 275 in fluid communication with the exhaust air inlet 270. The thermal control apparatus 200 can further include a second muffler stage 285 in fluid communication with the hot air outlet 240 and the first muffler stage 275. The thermal control apparatus 200 can further include an enclosure 290 housing the heat exchanger 250, wherein the vortex tube 210 and the exhaust air outlet 260 are located outside the enclosure 290.

Figure 4A:
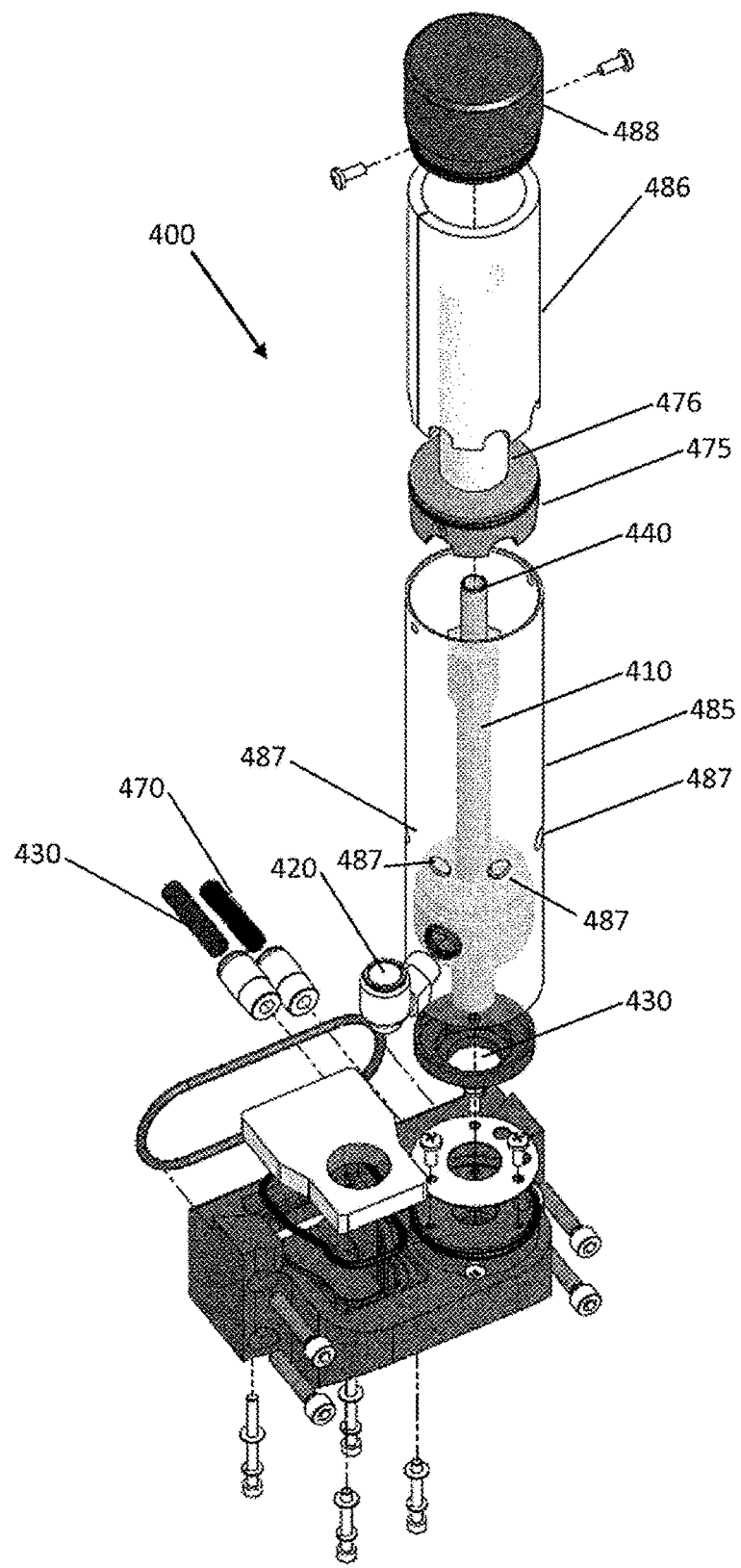
FIG. 4A is a perspective exploded view of an exemplary embodiment of a vortex tube according to the invention.

As shown in FIG. 4A, the thermal control apparatus 400 comprises a first muffler stage 475 that includes an inner cylinder 476 disposed around the vortex tube 410, the inner cylinder 476 being in fluid communication with the exhaust air inlet 470, such that the exhaust air flows through the inner cylinder 476 as described further below. The inner cylinder 476 can be concentric with the vortex tube 410. The apparatus 400 additionally comprises a second muffler stage 485 including an outer cylinder 486 in fluid communication with the hot air outlet 440. The outer cylinder 486 can be concentric with the inner cylinder 476. The outer cylinder 486 can include a foam cylinder, comprising, for example, temperature resistant foam insulation with sub-micron size pores. The second muffler stage 485 includes a plurality of outlet apertures 487 and a cap 488 that seals the end of the second muffler stage 485 forcing the exhaust air out through outlet apertures 487. The outlet apertures can have a diameter in a range of between 5 mm and 10 mm, such as 8 mm.

Figure 4B:
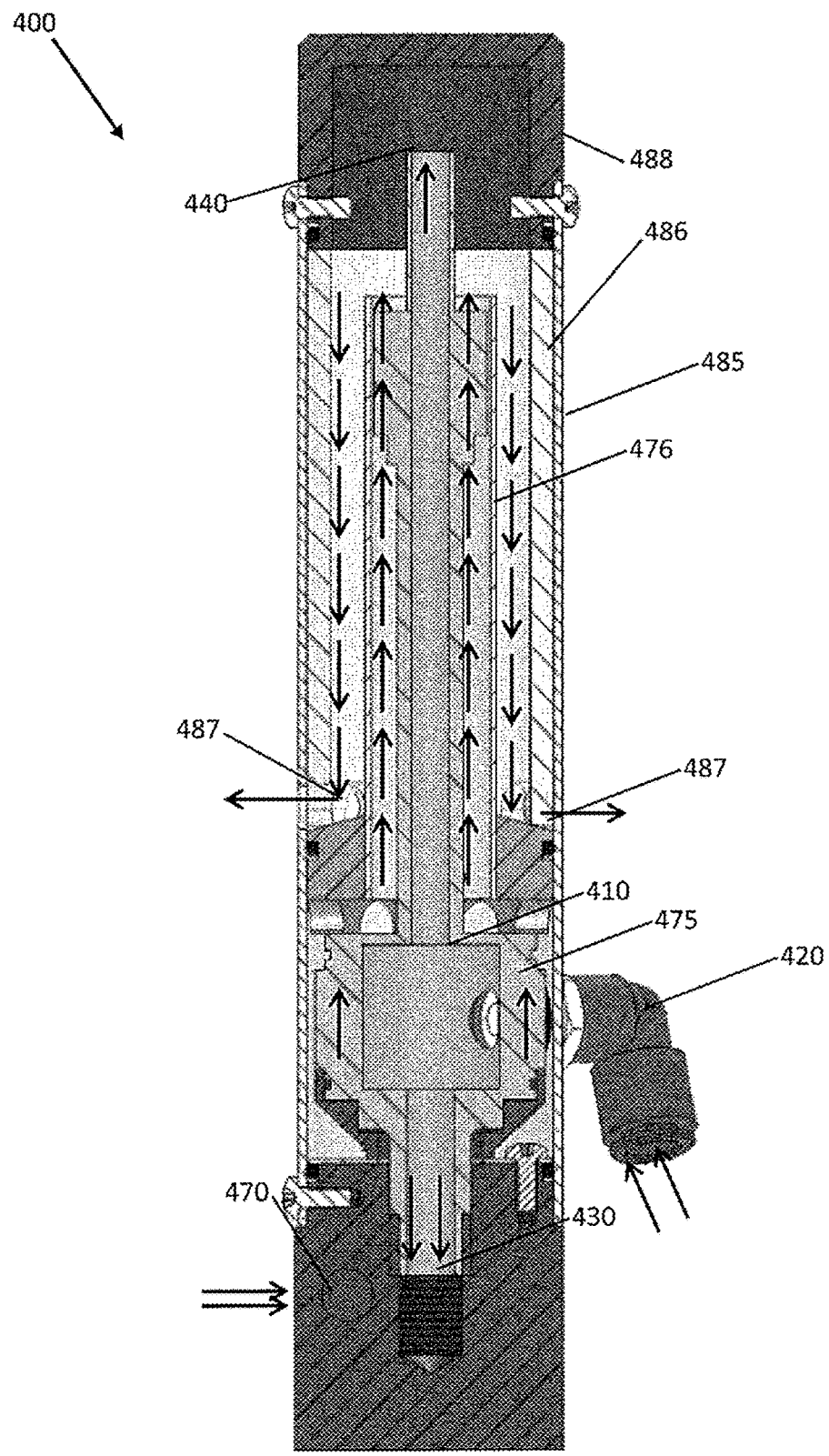
FIG. 4B is a cross section of an exemplary embodiment of a vortex tube according to the invention.

As shown in FIG. 4B, the exhaust air flows through the exhaust air inlet 470, around the vortex tube 410, thereby cooling the surface of the vortex tube 410, and through the inner cylinder 476 in a direction from the vortex tube inlet 420 toward the hot air outlet 440. The hot air and the exhaust air combine within the cap 488 and flow through the gap between the outer cylinder 486 and the inner cylinder 476 toward the outlet apertures 487. In an exemplary embodiment, the combined air can generate a noise level of less than or equal to 80 dBA during operation.

Figure 5:
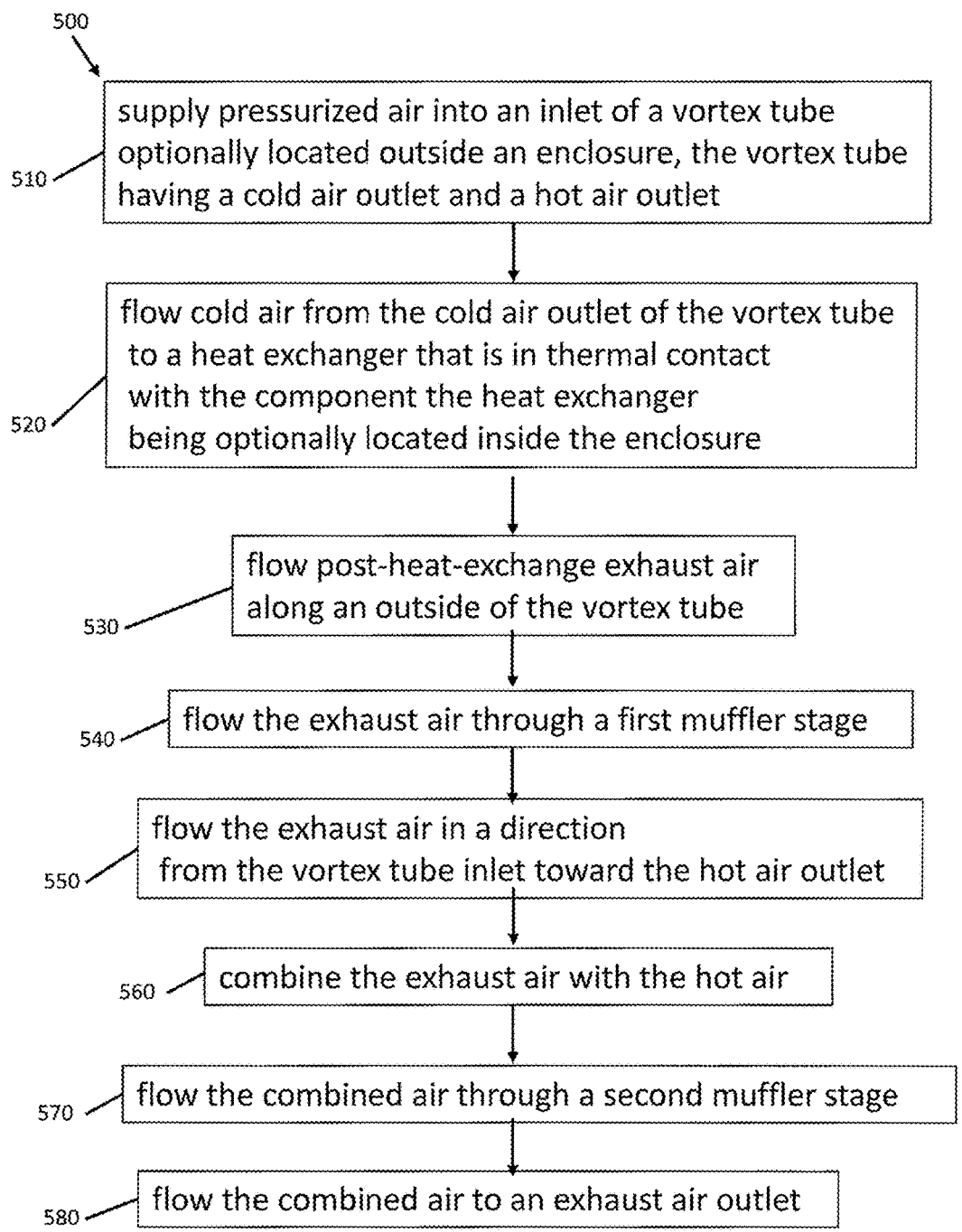
FIG. 5 is a flow chart of an exemplary embodiment of a method of controlling temperature of a component according to the invention.

In another embodiment shown in FIG. 5, a method of controlling temperature of a component 500 includes supplying at step 510 pressurized air into an inlet of a vortex tube having a cold air outlet and a hot air outlet, flowing at step 520 cold air from the cold air outlet of the vortex tube to a heat exchanger that is in thermal contact with the component, and thereby controlling the temperature of the component, flowing at step 530 post-heat-exchange exhaust air along an outside of the vortex tube, and combining at step 560 the exhaust air with the hot air. The method further includes flowing at step 580 the combined air to an exhaust air outlet.

In some embodiments, the method further includes flowing at step 540 the exhaust air through a first muffler stage including an inner cylinder disposed around the vortex tube, the inner cylinder being in fluid communication with the exhaust air inlet, such that the exhaust air flows through the inner cylinder. In certain embodiments, the method further includes flowing at step 550 the exhaust air through the inner cylinder in a direction from the vortex tube inlet toward the hot air outlet, and flowing at step 570 the combined air through a second muffler stage including an outer cylinder in fluid communication with the hot air outlet. In some embodiments, flowing the combined air can generate a noise level of less than or equal to 80 Dba, such as, for example, less than 75 dBA. In certain embodiments, the method further includes locating the heat exchanger in an enclosure, and locating the vortex tube and exhaust air outlet outside the enclosure.

Figure 6A:
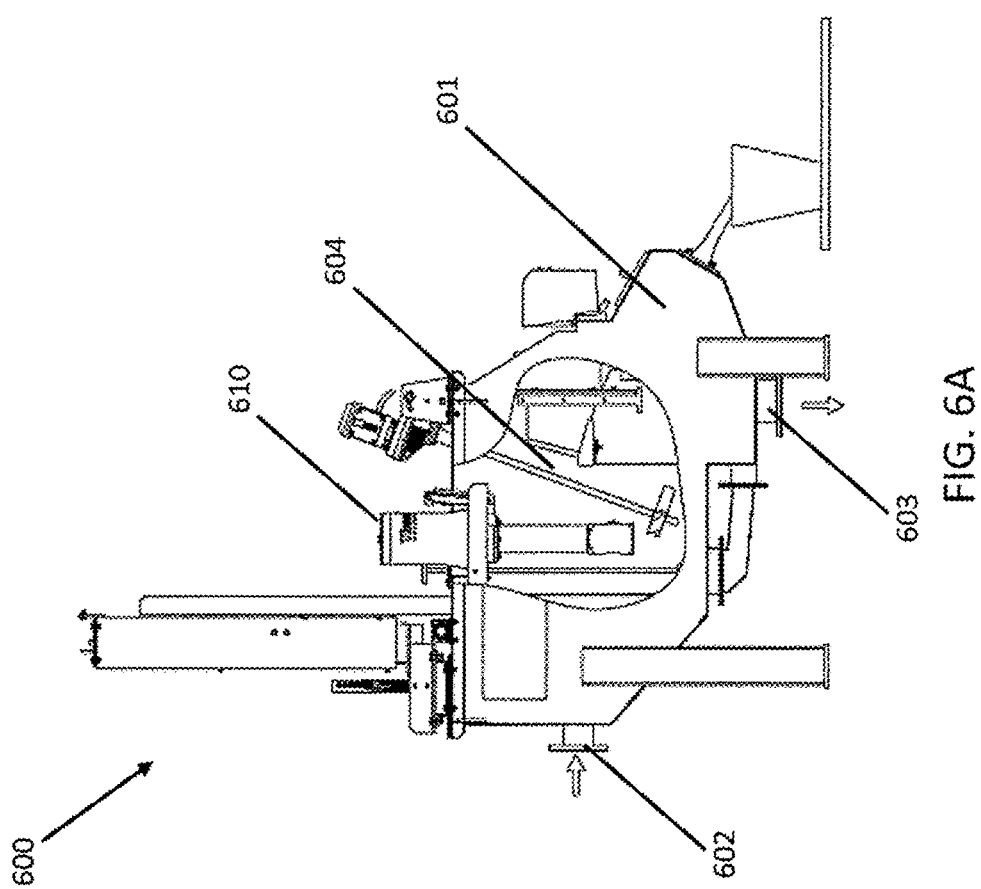
FIG. 6A is a schematic illustration of an online sampling and analysis station including an XRF immersion probe analyzer including an exemplary embodiment of a thermal control apparatus according to the invention.
Figure 6C:
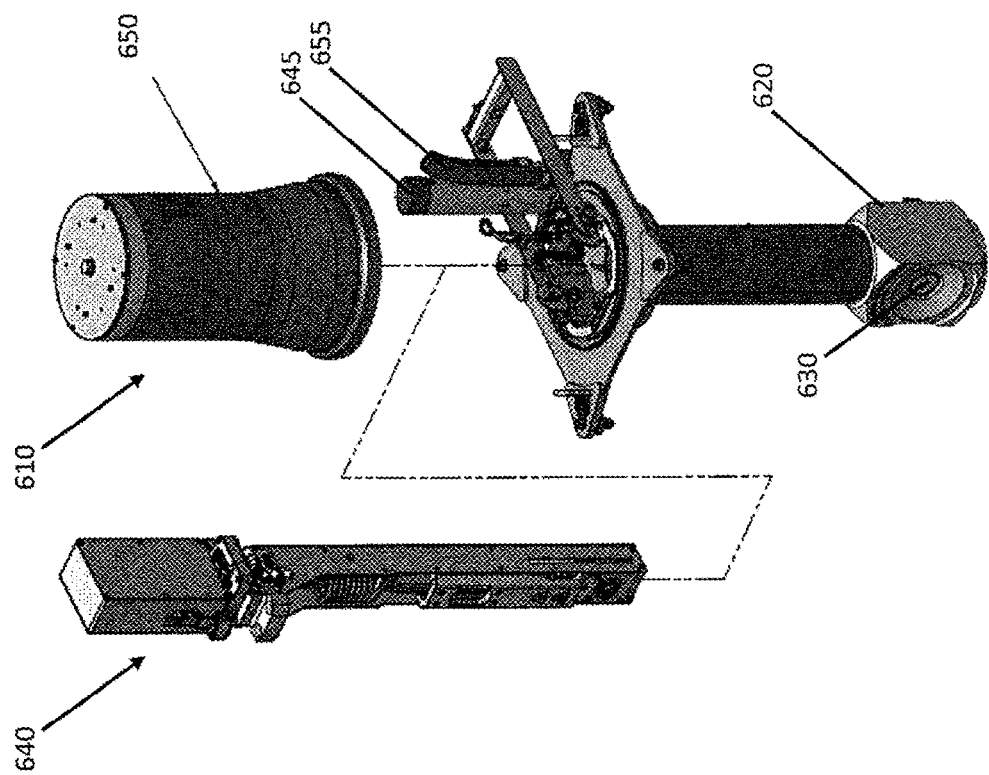
FIGS. 6B and 6C are perspective views of an XRF immersion probe analyzer including an exemplary embodiment of a thermal control apparatus according to the invention.
Figure 6B:
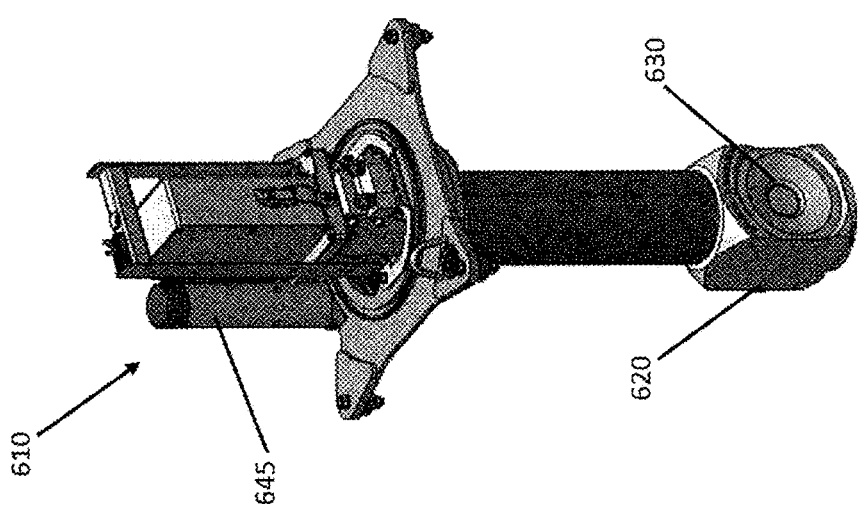

In yet another embodiment shown in FIG. 6A, an online sampling and analysis station 600 includes a housing 601 having a slurry inlet flange 602 and a slurry outlet flange 603, and a stirrer 604 that stirs the slurry within the housing 601 to present a homogeneous mixture to an XRF immersion probe analyzer 610. As shown in FIG. 6B, the XRF immersion probe analyzer 610 includes a probe head 620 immersible into and resistant to an ore slurry. The probe head 620 includes an X-ray transparent window 630, that is typically made of 50 µm thick Mylar. The probe 640 is sealed inside the XRF immersion probe analyzer 610 by cap 650 (shown in FIG. 6C). As shown in FIG. 6D, the probe 640 includes at least one X-ray source 660 (four X-ray sources 660a-660d are shown in FIG. 6D) that emits X-rays toward a sample through the window 630 (shown in FIGS. 6B and 6C), and a silicon drift X-ray fluorescence (XRF) detector 670 that detects X-ray radiation backscattered from the sample through the window 630, the silicon drift detector (SDD) having a hot side in thermal contact with a heat exchanger as described above. As shown in FIGS. 6B and 6C, the XRF immersion probe analyzer 610 further includes a vortex tube 645 having an inlet 655 adapted for connection with the pressurized air supply. The vortex tube, SDD, and heat exchanger are described above. The temperature of the hot side of the SDD can be controlled to a set temperature, such as 15° C.

OTHER EMBODIMENTS

A number of embodiments have been described. Nevertheless, it will be understood that various modifications may be made without departing from the spirit and scope of the disclosure. Accordingly, other embodiments are within the scope of the following claims.

What is claimed is:

1. A thermal control apparatus adapted for use with a pressurized air supply for controlling temperature of a component, the apparatus comprising:
   a. a vortex tube having an inlet adapted for connection with the pressurized air supply, a cold air outlet, and a hot air outlet; and
   b. a heat exchanger in fluid communication with the cold air outlet of the vortex tube, the heat exchanger being in thermal contact with the component and thereby controlling the temperature of the component, the heat exchanger further including a post-heat-exchange exhaust air outlet in fluid communication with an exhaust air inlet adapted to direct the exhaust air along an outside of the vortex tube.

2. The thermal control apparatus of claim 1, additionally comprising a first muffler stage including an inner cylinder disposed around the vortex tube, the inner cylinder being in fluid communication with the exhaust air inlet, such that the exhaust air flows through the inner cylinder.

3. The thermal control apparatus of claim 2, wherein the inner cylinder is concentric with the vortex tube.

4. The thermal control apparatus of claim 2, wherein the exhaust air flows through the inner cylinder in a direction from the vortex tube inlet toward the hot air outlet, the apparatus additionally comprising a second muffler stage including an outer cylinder in fluid communication with the hot air outlet.

5. The thermal control apparatus of claim 4, wherein the outer cylinder is concentric with the inner cylinder.

6. The thermal control apparatus of claim 4, wherein the outer cylinder includes a foam cylinder.

7. The thermal control apparatus of claim 4, wherein the outer cylinder further includes a plurality of outlet apertures.

8. The thermal control apparatus of claim 7, wherein the outlet apertures have a diameter in a range of between 5 mm and 10 mm.

9. The thermal control apparatus of claim 8, wherein the diameter of the outlet apertures is 8 mm.

10. The thermal control apparatus of claim 1, further including an enclosure housing the heat exchanger, wherein the vortex tube and exhaust air outlet are located outside the enclosure.

11. The thermal control apparatus of claim 1, wherein the component is a hot side of a silicon drift detector.

12. The thermal control apparatus of claim 11, wherein the temperature of the hot side of the silicon drift detector is controlled to a set temperature.

13. The thermal control apparatus of claim 12, wherein the set temperature is 15° C.

14. A method of controlling temperature of a component, the method comprising:
   a. supplying pressurized air into an inlet of a vortex tube having a cold air outlet and a hot air outlet;
   b. flowing cold air from the cold air outlet of the vortex tube to a heat exchanger that is in thermal contact with the component, and thereby controlling the temperature of the component;
   c. flowing post-heat-exchange exhaust air along an outside of the vortex tube; and
   d. combining the exhaust air with the hot air and flowing the combined air to an exhaust air outlet.

15. The method of claim 14, further including flowing the exhaust air through a first muffler stage including an inner cylinder disposed around the vortex tube, the inner cylinder being in fluid communication with the exhaust air inlet, such that the exhaust air flows through the inner cylinder.

16. The method of claim 15, further including flowing the exhaust air through the inner cylinder in a direction from the vortex tube inlet toward the hot air outlet, and flowing the combined air through a second muffler stage including an outer cylinder in fluid communication with the hot air outlet.

17. The method of claim 14, wherein flowing the combined air generates a noise level of less than or equal to 80 dBA.

18. The method of claim 14, further including locating the heat exchanger in an enclosure, and locating the vortex tube and exhaust air outlet outside the enclosure.

19. An XRF immersion probe analyzer comprising:
   a. a probe head immersible into and resistant to an ore slurry, the probe head including an X-ray transparent window;
   b. a probe including:
      i. at least one X-ray source that emits X-rays toward a sample through the window;
      ii. a silicon drift X-ray fluorescence (XRF) detector that detects X-ray radiation backscattered from the sample through the window, the silicon drift detector (SDD) having a hot side;
   c. a vortex tube having an inlet adapted for connection with the pressurized air supply, a cold air outlet, and a hot air outlet; and
   d. a heat exchanger in fluid communication with the cold air outlet of the vortex tube, the heat exchanger being in thermal contact with the hot side of the SDD and thereby controlling the temperature of the hot side of the SDD, the heat exchanger further including a post-heat-exchange exhaust air outlet in fluid communication with an exhaust air inlet adapted to direct the exhaust air along an outside of the vortex tube.

20. The XRF immersion probe analyzer of claim 19, wherein the temperature of the hot side of the SDD is controlled to a set temperature.

21. The XRF immersion probe analyzer of claim 20, wherein the set temperature is 15° C.

22. The XRF immersion probe analyzer of claim 19, additionally comprising a first muffler stage including an inner cylinder disposed around the vortex tube, the inner cylinder being in fluid communication with the exhaust air inlet, such that the exhaust air flows through the inner cylinder.

23. The XRF immersion probe analyzer of claim 22, wherein the inner cylinder is concentric with the vortex tube.

24. The XRF immersion probe analyzer of claim 22, wherein the exhaust air flows through the inner cylinder in a direction from the vortex tube inlet toward the hot air outlet, the apparatus additionally comprising a second muffler stage including an outer cylinder in fluid communication with the hot air outlet.

25. The XRF immersion probe analyzer of claim 24, wherein the outer cylinder is concentric with the inner cylinder.

26. The XRF immersion probe analyzer of claim 25, wherein the outer cylinder includes a foam cylinder.

27. The XRF immersion probe analyzer of claim 24, wherein the outer cylinder further includes a plurality of outlet apertures.

28. The XRF immersion probe analyzer of claim 27, wherein the outlet apertures have a diameter in a range of between 5 mm and 10 mm.

29. The XRF immersion probe analyzer of claim 28, wherein the diameter of the outlet apertures is 8 mm.

30. The XRF immersion probe analyzer of claim 19, further including an enclosure housing the heat exchanger, wherein the vortex tube and exhaust air outlet are located outside the enclosure.

* * * * *